(12) United States Patent
Cline et al.

(10) Patent No.: US 6,656,495 B2
(45) Date of Patent: *Dec. 2, 2003

(54) CORN, CALLUS AND WART REMOVING PADS

(75) Inventors: Mojgan Cline, Memphis, TN (US); Charles E. Lundy, Jr., Germantown, TN (US); Ronald Feret, Memphis, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/218,648

(22) Filed: Aug. 14, 2002

(65) Prior Publication Data

US 2002/0197305 A1 Dec. 26, 2002

Related U.S. Application Data

(63) Continuation of application No. 09/628,633, filed on Jul. 31, 2000.

(51) Int. Cl.$^7$ .......................... A61L 15/16; A01N 37/00
(52) U.S. Cl. ........................ 424/446; 514/558
(58) Field of Search ................................ 424/443, 446, 424/447, 448, 449; 514/558

(56) References Cited

U.S. PATENT DOCUMENTS 5,547,989 A * 8/1996 Chamness ................ 514/558
6,471,986 B1 * 10/2002 Cline et al. ................ 424/446

FOREIGN PATENT DOCUMENTS

DE         4 001 034        * 7/1991

* cited by examiner

Primary Examiner—Thurman K. Page
Assistant Examiner—Sharon Howard
(74) Attorney, Agent, or Firm—Robert J. Lipka

(57) ABSTRACT

A wart, callus and/or corn removing pad including a layer of hydrocolloid adhesive material having a periphery and an underside, a medicated plaster secured centrally to the underside of the layer of hydrocolloid adhesive material and including salicylic acid therein, a barrier layer interposed between the medicated plaster and the layer of hydrocolloid adhesive material to prevent diffusion of the salicylic acid in the medicated plaster to the layer of hydrocolloid adhesive material, an outer layer secured to the layer of hydrocolloid material, the outer layer at least having a border extending outwardly of the layer of hydrocolloid adhesive material, the border having an underside, a layer of adhesive material on the underside of the border, a release liner releasably secured to the underside of the hydrocolloid adhesive layer, and a paper release tab releasably secured to an upper surface of at least one of the hydrocolloid adhesive layer and the outer layer at one side thereof.

27 Claims, 1 Drawing Sheet

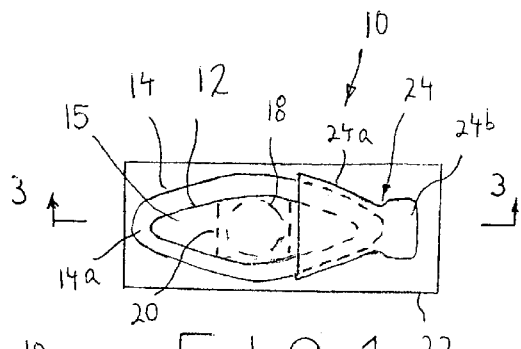
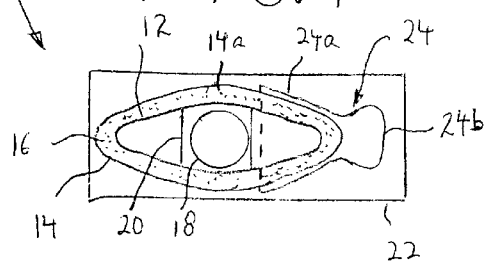
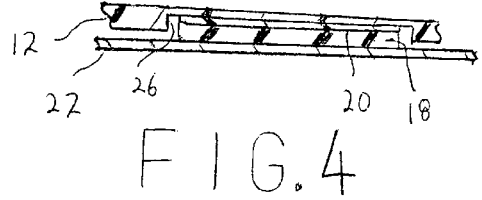
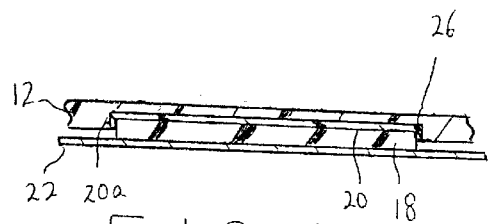
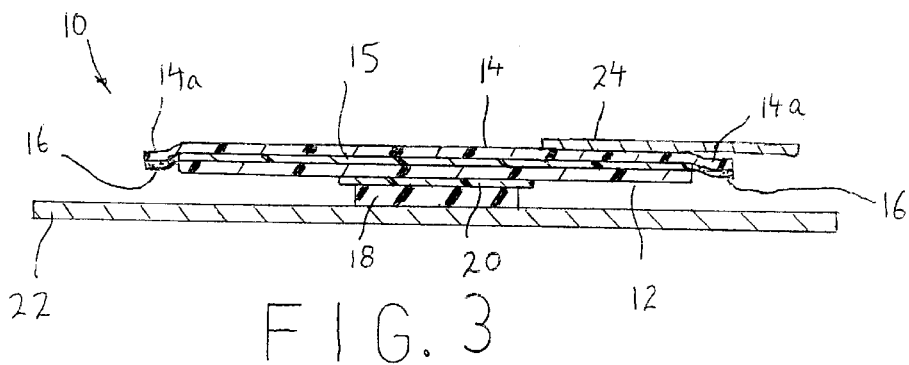

CORN, CALLUS AND WART REMOVING PADS

This application claims benefit of priority to co-pending U.S. patent application Ser. No. 09/628,633.

BACKGROUND OF THE INVENTION

The present invention relates generally to pads for corns, calluses and warts, and more particularly, to an improved corn, callus and wart removing pad.

Corns are a painful type of hyperkeratosis, found principally over prominent toe joints and between toes. There are two common types of corns: Heloma Durum and Heloma Molle. Heloma Durum (hard corn) is a hyperkeratotic lesion which appears over a bony prominence and may have a deep nucleus. These corns are normally very tender and painful. The Heloma Molle (soft corn) is a hyperkeratotic lesion which is found between the toes. The soft corn results from pressure exerted between adjacent toes and is soft due to moisture between the toes.

A callus may be a diffuse or circumscribed area of hyperkeratosis at a site of repeated pressure and friction. In cases where there is a forefoot imbalance the plantar callus may be found where the metatarsal heads are most prominent.

Plantar warts are simple papillomas caused by a virus. Plantar warts differ from calluses and are not necessarily found over bony prominences. They may be sharply circumscribed with their edges clearly demarcated from the surrounding skin. Their center is darker than the surrounding skin and their may have a mosine appearance. Warts are usually painful to squeezing and often exhibit pain from the pressure of walking.

Medicated pads are known for placement over corns, calluses and warts, and which contain an ingredient, such as 40% salicylic acid by weight in a rubber based vehicle, for removing corns, calluses and warts. For example, such pads are sold by Schering-Plough Healthcare Products, Inc. of Memphis, Tenn. under the house trademark "DR. SCHOLL'S", and under the particular trademarks "CLEAR AWAY" and "ONE STEP".

Specifically, with such known pads, there is a relatively thick center cushion formed of ethylene foam or ethylene vinyl acetate (EVA), polyethylene or like material having a circular opening, and an elongated vinyl film secured to the upper surface of the center cushion section and extending outwardly from opposite sides thereof. An adhesive is applied to the lower surfaces of the entire thick center cushion section and the elongated portions of the vinyl film that extend outwardly from opposite sides of the thick center cushion section. In effect, the shape is similar to a conventional adhesive bandage, but with adhesive material also provided on the lower surface of the center cushion.

A disk containing the salicylic acid is provided in the recess, and is separated from the remainder of the center cushion and from the vinyl strip by a barrier layer. A release liner is provided on the underside of the pad, and extends along the entire center cushion and vinyl film. Also, a paper release tab is releasably secured to the lower surface of one free end of the vinyl strip.

In use, a person removes the release liner, thereby exposing the adhesive layer applied to the lower surfaces of the entire thick center cushion and the elongated portions of the vinyl film that extend outwardly from opposite sides of the thick center cushion. The lower surfaces of the entire thick center cushion and the elongated portions of the vinyl film that extend outwardly from opposite sides of the thick center cushion are then secured to the person's skin, such that the medicated disk covers the corn, wart or callus to be removed. The paper release tab is then removed.

However, such product has a generally high profile, that is, a relatively large cross-sectional thickness. Also, this arrangement requires adhesive to be applied to both the lower surfaces of the entire thick center cushion and the elongated portions of the vinyl film that extend outwardly from opposite sides of the thick center cushion.

More importantly, the center cushion is water impermeable. When the person perspires, moisture and liquid can form an interface layer between the medicated disk and the skin containing the corn, callus or wart. Also, such interface layer tends to weaken the adhesive, so that the pad tends to fall from the skin after a relatively short period of time in the presence of such liquid interface layer.

A further problem with such product is that the salicylic acid tends to evaporate and be lost to the environment over time. For example, in tests performed in accelerated aging conditions under a temperature of 40° C. and 75% relative humidity, over a three month period, for a product starting with 42% salicylic acid by weight, only 36–37% salicylic acid by weight remained. This represents a very large loss of medicament.

It is known to provide bandages out of other materials. For example, it is known to provide trauma bandages made from a hydrocolloid adhesive layer. However, these trauma bandages do not include any transdermal device containing any keratolytic agent (skin removing) or other medicaments.

SUMMARY OF THE INVENTION

Accordingly, it is an object of the present invention to provide a medicated pad that overcomes the problems with the aforementioned prior art.

It is another object of the present invention to provide a medicated pad particularly adapted for removing warts, calluses and corns.

It is still another object of the present invention to provide a medicated pad which uses less adhesive than conventional medicated pads.

It is yet another object of the present invention to provide a medicated pad in which the center hydrocolloid adhesive layer performs the dual function of an adhesive layer and a cushion.

It is a further object of the present invention to provide a medicated pad in which adhesion is increased in the presence of a liquid.

It is a still further object of the present invention to provide a medicated pad which will adhere to a person's skin for a longer period of time.

It is a yet further object of the present invention to provide a medicated pad in which less medicament will be lost to the environment.

It is another object of the present invention to provide a medicated pad having a longer shelf life than conventional medicated pads.

In accordance with an aspect of the present invention, a medicated pad includes a center cushion layer having adhesive and liquid absorbing properties, said center cushion layer having a periphery and an underside, a medicated plaster secured to the underside of the center cushion layer, a barrier layer interposed between the medicated plaster and the center cushion layer to prevent diffusion of any medicament in the medicated plaster to the center cushion layer, an outer layer secured to the center cushion layer, the outer layer at least having a border extending outwardly of the layer of center cushion layer, the border having an underside, and a layer of adhesive material on the underside of the border. Preferably, the medicament includes salicylic acid, and the medicated plaster is secured at a substantially central position of the center cushion layer.

The barrier layer is made from a material selected from the group consisting of polyester film, polypropylene and polyolefin films.

A release liner is releasably secured to the underside of the center cushion layer. The release liner is made from a material selected from the group consisting of polyester film, polypropylene film, polyethylene film, polyolefin films, paper and polyethylene/paper laminates or film/paper laminates.

A release tab is releasably secured to an upper surface at one side of at least one of the center cushion layer and the outer layer. The release tab is made from a paper material or polymer film.

The center cushion layer may also include a recess at the underside thereof, and the barrier layer and the medicated plaster are positioned at least partially in the recess. In one embodiment, the recess includes a side wall and a bottom wall, the barrier layer is interposed between the bottom wall and the medicated plaster, and the medicated plaster is spaced apart from the side wall of the recess. In another embodiment, the recess includes a side wall and a bottom wall, and the barrier layer is interposed between the side and bottom walls of the recess and the medicated plaster.

In accordance with another aspect of the present invention, a medicated pad includes a layer of hydrocolloid adhesive material having a periphery and an underside, a medicated plaster secured to the underside of the layer of hydrocolloid adhesive material, a barrier layer interposed between the medicated plaster and the layer of hydrocolloid adhesive material to prevent diffusion of any medicament in the medicated plaster to the layer of hydrocolloid adhesive material, an outer layer secured to the layer of hydrocolloid adhesive material, the outer layer at least having a border extending outwardly of the center cushion layer, the border having an underside, and a layer of adhesive material on the underside of the border.

In accordance with still another aspect of the present invention, a medicated pad includes a layer of hydrogel adhesive material having a periphery and an underside, a medicated plaster secured to the underside of the layer of hydrogel adhesive material, a barrier layer interposed between the medicated plaster and the layer of hydrogel adhesive material to prevent diffusion of any medicament in the medicated plaster to the layer of hydrogel adhesive material, an outer layer secured to the layer of hydrogel adhesive material, the outer layer at least having a border extending outwardly of the center cushion layer, the border having an underside, and a layer of adhesive material on the underside of the border.

The above and other features of the invention will become readily apparent from the following detailed description thereof which is to be read in connection with the accompanying drawings.

BRIEF DESCRIPTION OF THE DRAWINGS

FIG. 1 is a top plan view of a medicated pad according to the present invention;

FIG. 2 is a bottom plan view of the medicated pad of FIG. 1;

FIG. 3 is a cross-sectional view of the medicated pad of FIG. 1, taken along line 3—3 thereof;

FIG. 4 is a cross-sectional view similar to FIG. 3 of a medicated pad according to a second embodiment of the present invention; and FIG. 5 is a cross-sectional view similar to FIG. 3 of a medicated pad according to a third embodiment of the present invention.

DETAILED DESCRIPTION

Referring to the drawings in detail, and initially to FIGS. 1–3, a pad 10 according to a first embodiment of the present invention for removing corns, calluses and warts, includes a center cushion layer 12 of a material having adhesive and liquid absorbing qualities. In this regard, a preferred material of layer 12 is a hydrocolloid adhesive material having a preferred thickness in the range of 0.001 inch (1 mil) to 0.050 inch (50 mils), with a most preferred thickness of 0.018 inch (18 mils). A suitable hydrocolloid adhesive material is sold by Avery Dennison Corp. of Painesville, Ohio under the designation #2190H. An alternative material is a hydrogel adhesive having a preferred thickness in the range of 0.001 inch (1 mil) to 0.050 inch (50 mils), with a most preferred thickness of 0.020 inch (20 mils). Hereinafter, this layer, for ease of explanation, will be referred to as a hydrocolloid adhesive layer.

Preferably, when used as a corn remover, layer 12 has the shape of a rhombus with a greatest length of about 1.375 inches and a greatest width of about 0.50 inch. However, hydrocolloid adhesive layer 12 will have different configurations and dimensions depending upon the particular application, and the specific shape and dimensions are not relevant to the present invention.

Hydrocolloid adhesive layer 12 has properties that are moderately adhesive, and when heated, provides greater adhesive properties. Thus, when placed on a person's skin, hydrocolloid adhesive layer 12 will stick to the person's skin, and as the person's body temperature heats up hydrocolloid adhesive layer 12, the adhesive activity of hydrocolloid adhesive layer will increase. This means that there is no need to provide a separate adhesive layer on the underside of hydrocolloid adhesive layer 12. Therefore, hydrocolloid adhesive layer 12 performs the dual function of a cushioning layer and an adhesive layer.

It will be appreciated that hydrocolloid adhesive layer 12 is liquid absorbent. This means that, as a person perspires, the moisture and water are absorbed by hydrocolloid adhesive layer 12. As a result, as a person perspires, there is no liquid interface layer formed between hydrocolloid adhesive layer 12 and the person's skin. This means that there is no deterioration of the adhesive quality of hydrocolloid adhesive layer 12 in the presence of moisture and/or water, so that the present invention will stay on a person's skin for a longer period of time. In fact, the absorption of water actually increases the adhesion of hydrocolloid adhesive layer 12 to the person's skin. Specifically, in the presence of water, hydrocolloid adhesive layer 12 forms a hydrogel layer which is an adhesive that increases the adhesive quality of hydrocolloid adhesive layer 12.

However, in order to provide an initial good adhesive quality prior to hydrocolloid adhesive layer 12 being heated, an outer layer 14 is secured to the upper surface of hydrocolloid adhesive layer 12. Outer layer 14 can have a substantially hollow rhombus shape, but preferably, has a solid rhombus shape which merely overlays on top of hydrocolloid adhesive layer 12. In any event, when used as a corn remover, the outer periphery of outer layer 14 forms a border 14a which preferably has a substantially rhombus shape which is the same as that of hydrocolloid adhesive layer 12, but of greater dimensions. For example, the rhombus of outer layer 14 can have a greatest length of about 1.625 inches and a greatest width of about 0.75 inch. However, outer layer 14 is not limited by this configuration or dimensions. Outer layer 14 can be made from any suitable material, including but not limited to polyvinyl chloride (PVC), polyurethane, polyethylene and polyolefin, and has a preferred thickness in the range of 0.0005 inch (0.5 mil) to 0.010 inch (10 mils), but is preferably made from a clear polyurethane film, sold by 3M Inc. of Minneapolis, Minn. under the designation #MSX 5527, with a most preferred thickness of 0.002 inch (2 mils).

Border 14a of outer layer 14 has its lower surface coated with an adhesive layer 16. Thus, when pad 10 is initially placed on a person's skin, adhesive layer 16 will hold pad 10 securely thereon. Subsequently, hydrocolloid adhesive layer 12 will heat up, thereby increasing the adhesive characteristics thereof, and further securely and releasably holding pad 10 in such position.

It will be appreciated that pad 10 according to the present invention uses one less coat of adhesive than the prior art "ONE STEP" pad since hydrocolloid adhesive layer 12 has an adhesive quality itself. Because of hydrocolloid adhesive layer 12, pad 10 stays adhered to a person's skin longer than the aforementioned "ONE STEP" pad.

Because of the adhesive quality of hydrocolloid adhesive layer 12, when shipped by manufacturers of the same, a top layer 15 is generally applied thereto, for example, a polyester film, polyethylene film, polyurethane or the like with a range of thickness between 0.0001 inch (0.1 mil) and 0.010 inch (10 mils). Preferably, such top layer 15 is a clear polypropylene film having a thickness of 0.00075 inch (0.75 mils).

In order to provide a beneficial keratolytic (skin removing) agent, for example, 40% salicylic acid by weight, a medicated plaster 18 is provided. Specifically, medicated plaster 18 is preferably made of a synthetic or natural rubber based matrix with 40% salicylic acid by weight. In such case, as is well known, the salicylic acid is mixed with a rubber mixture, a plasticizer and a tackifier, to form stiff rubber medicated plaster 18. Although a disk shape is shown, the present invention is not limited thereby, and medicated plaster 18 can have any shape. Medicated plaster 18 preferably has a thickness in the range of 0.010 inch (10 mils) to 0.050 inch (50 mils), with a most preferred thickness of in the range of 0.020 inch (20 mils) to 0.025 inch (25 mils).

Medicated plaster 18 is secured to the underside of hydrocolloid adhesive layer 12, preferably at a center position thereof. In this manner, medicated plaster 18 is placed directly on the skin portion corresponding to the wart, corn or callus, and is surrounded by hydrocolloid adhesive layer 12.

In order to prevent migration of the salicylic acid into hydrocolloid adhesive layer 12, which would occur if medicated plaster 18 were directly in contact with hydrocolloid adhesive layer 12, a barrier layer 20 is connected between hydrocolloid adhesive layer 12 and medicated plaster 18. Barrier layer 20 prevents migration of the salicylic acid from medicated plaster 18 to hydrocolloid adhesive layer 12. Barrier layer 20 can be made from any suitable material including, but not limited to, a polyester film, polypropylene and polyolefin films. Preferably, barrier layer 20 has a thickness in the range of 0.00025 inch (0.25 mil) to 0.002 inch (2 mils), and is most preferably a clear polyester film sold by Scapa Tapes Inc. of Windsor, Conn. under designation number RX529PX, with a thickness of 0.00005 inch (0.5 mil).

It has also been determined that there is less evaporation and loss to the environment of the salicylic acid with pad 10 than with the aforementioned "ONE STEP" pad. Specifically, in three month tests in accelerated aging conditions under a temperature of 40 C. and 75% relative humidity, with medicated plaster 18 having 42% salicylic acid by weight, there was a loss of less than one percent (1%). With the same starting tests with the aforementioned "ONE STEP" pad, the amount of salicylic acid dropped from 42% by weight to between 36% and 37% by weight. This result is surprising since hydrocolloid adhesive layer 12 is water absorbent, and it would be expected that the salicylic acid would be absorbed after evaporation into hydrocolloid adhesive layer. However, the direct opposite occurred, and pad 10 remained more stable over time than the aforementioned "ONE STEP" pad, that is, with less loss of the salicylic acid.

In addition, a release liner 22 is releasably secured to the underside of pad 10, and particularly, in covering relation to the underside or lower surfaces of hydrocolloid adhesive layer 12, outer layer 14 with adhesive layer 16 thereon, and medicated plaster 18. Release liner 22 serves as a protective layer until pad 10 is to be used. Although release liner 22 is shown in a rectangular configuration, the present invention is not limited by this shape. Release liner 22 is preferably transparent and can be made from any suitable material including, but not limited to polyester film, polypropylene film, polyethylene film and polyolefin films, with a preferred range of thickness from 0.002 inch (2 mils) to 0.010 inch (10 mils), and a most preferred thickness of 0.005 inch (5 mils). Alternatively, release liner 22 can be made from a heavy weight paper, polyethylene/paper laminates or film/paper laminates, with a preferred weight range of 30 to 150 pounds per ream, and with a preferred weight of 90 pounds per ream. The preferred material, however, for release liner 22 is a silicone coated polyester film sold by Daubert Coated Products Inc. of Dixon, Ill. under the designation 4020 HS and having a thickness of 0.005 inch (5 mils).

Lastly, pad 10 includes a paper release tab 24 releasably secured to the upper surface of hydrocolloid adhesive layer 12 and/or outer layer 14 at one side thereof. For a corn remover, paper release tab 24 preferably has a trapezoidal section 24a that is releasably secured by the adhesive quality of hydrocolloid adhesive layer 12 on the upper surface of the same, and a substantially rectangular section 24b that extends out from hydrocolloid adhesive layer 12 and merely overlies release liner 22. Paper release tab 24 can be made from any suitable stock paper such as that sold by Simpson Paper Company of Anderson, Calif. under the designation 100# C1s Litho Facer, and preferably has a weight in the range of 30 to 150 pounds per ream, with a most preferred weight of 100 pounds per ream. Alternatively, release tab 24 can be made from a polymer film.

Although FIGS. 1 and 2 show the different elements in substantially the correct shapes and dimensions of the preferred embodiment for a corn remover, the thicknesses of the layers in FIG. 4 are not shown in the correct dimensions in order to better illustrate the present invention.

In use, a person pulls up on substantially rectangular section 24b of release tab 24 with one hand, while holding the portion of release liner 22 immediately below with the other hand. This functions to remove pad 10 from release liner 22. Pad 10 is then placed on the person's skin, with medicated plaster 18 immediately above the corn, callus or wart to be removed. Adhesive layer 16 functions to secure pad 10 thereon. As the skin heats up, the adhesive quality of hydrocolloid adhesive layer 12 increases, further adding to the securement of pad 10 to the person's skin. Paper release tab 24 is then pulled up. At this time, paper release tab 24 is detached from pad 10, leaving pad 10 on the person's skin.

It will therefore be appreciated that pad 10 uses less adhesive than conventional medicated pads, that is, with only a small adhesive layer 16 at the outer periphery thereof. This is because hydrocolloid adhesive layer 12 performs the dual function of an adhesive layer and a cushion. Also, in the presence of a liquid and/or moisture, hydrocolloid adhesive layer 12 absorbs the same, with the result that the adhesive qualities are increased. This means that pad 10 will adhere to a person's skin for a longer period of time than conventional medicated pads.

Another advantage with the present invention is that less medicament will be lost to the environment. This is due to the combination of hydrocolloid adhesive layer 12 with medicated plaster 16. As a result, pad 10 will have a longer shelf life than conventional medicated pads.

It will be appreciated that various changes and modifications within the scope of the present invention can be provided. For example, the underside of hydrocolloid adhesive layer 12 can be provided with a recess 26 at the center thereof, and barrier layer 20 and medicated plaster 18 can be provided in recess 26 in spaced relation to the side walls of recess 26, as shown in FIG. 5. In such case, a portion of medicated plaster 18 extends out from recess 26 to a lower height than the lower surface of hydrocolloid adhesive layer 12.

Alternatively, barrier layer 20 can additionally include a side wall 20a itself between the side walls of recess 26 and the outer peripheral side of medicated plaster 18, as shown in FIG. 6.

Although the present invention has been discussed in relation to a pad for removing warts, corns and calluses and containing salicylic acid as the keratolytic agent, the present invention can be used with any other keratolytic agent and/or medicament, such as an antibiotic agent, antimicrobial agent, antifungal agent or the like.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

Parts Designator

10 pad
12 hydrocolloid adhesive layer
14 outer layer
14a border
15 top layer
16 adhesive layer
18 medicated plaster
20 barrier layer
20a side wall
22 release liner
24 paper release tab
24a trapezoidal section
24b rectangular section
26 recess

What is claimed is:

1. A medicated pad comprising:
   a center cushion layer having adhesive and liquid absorbing properties, said center cushion layer having a periphery and an underside,
   a medicated plaster secured to the underside of said center cushion layer,
   a barrier layer interposed between said medicated plaster and said center cushion layer to prevent diffusion of any medicament in said medicated plaster to said center cushion layer,
   an outer layer secured to said center cushion layer, said outer layer at least having a border extending outwardly of said center cushion layer, said border having an underside, and
   a layer of adhesive material on the underside of said border.

2. A medicated pad according to claim 1, wherein said medicament includes salicylic acid.

3. A medicated pad according to claim 1, wherein said medicated plaster is secured at a substantially central position of said center cushion layer.

4. A medicated pad according to claim 1, wherein said barrier layer is made from a material selected from the group consisting of polyester film, polypropylene and polyolefin films.

5. A medicated pad according to claim 1, further comprising a release liner releasably secured to the underside of said center cushion layer.

6. A medicated pad according to claim 5, wherein said release liner is made from a material selected from the group consisting of polyester film, polypropylene film, polyethylene film, polyolefin films, paper and polyethylene/paper laminates or film/paper laminates.

7. A medicated pad according to claim 1, further comprising a release tab releasably secured to an upper surface at one side of at least one of said center cushion layer and said outer layer.

8. A medicated pad according to claim 7, wherein said release tab is made from a material selected from the group of a paper material and a polymer film.

9. A medicated pad according to claim 1, wherein said center cushion layer includes a recess at the underside thereof, and said barrier layer and said medicated plaster are positioned at least partially in said recess.

10. A medicated pad according to claim 9, wherein said recess includes a side wall and a bottom wall, said barrier layer is interposed between said bottom wall and said medicated plaster, and said medicated plaster is spaced apart from said side wall of said recess.

11. A medicated pad according to claim 9, wherein said recess includes a side wall and a bottom wall, and said barrier layer is interposed between said side and bottom walls of said recess and said medicated plaster.

12. A medicated pad comprising:
   a layer of hydrocolloid adhesive material having a periphery and an underside,
   a medicated plaster secured to the underside of said layer of hydrocolloid adhesive material,
   a barrier layer interposed between said medicated plaster and said layer of hydrocolloid adhesive material to prevent diffusion of any medicament in said medicated plaster to said layer of hydrocolloid adhesive material,
   an outer layer secured to said layer of hydrocolloid adhesive material, said outer layer at least having a border extending outwardly of said center cushion layer, said border having an underside, and a layer of adhesive material on the underside of said border.

13. A medicated pad according to claim 12, wherein said medicament includes salicylic acid.

14. A medicated pad according to claim 12, wherein said medicated plaster is secured at a substantially central position of said layer of hydrocolloid adhesive material.

15. A medicated pad according to claim 12, further comprising a release liner releasably secured to the underside of said layer of hydrocolloid adhesive material.

16. A medicated pad according to claim 12, further comprising a release tab releasably secured to an upper surface at one side of at least one of said layer of hydrocolloid adhesive material and said outer layer.

17. A medicated pad according to claim 12, wherein said layer of hydrocolloid adhesive material includes a recess at the underside thereof, and said barrier layer and said medicated plaster are positioned at least partially in said recess.

18. A medicated pad according to claim 17, wherein said recess includes a side wall and a bottom wall, said barrier layer is interposed between said bottom wall and said medicated plaster, and said medicated plaster is spaced apart from said side wall of said recess.

19. A medicated pad according to claim 17, wherein said recess includes a side wall and a bottom wall, and said barrier layer is interposed between said side and bottom walls of said recess and said medicated plaster.

20. A medicated pad comprising:

a layer of hydrogel adhesive material having a periphery and an underside, a medicated plaster secured to the underside of said layer of hydrogel adhesive material, a barrier layer interposed between said medicated plaster and said layer of hydrogel adhesive material to prevent diffusion of any medicament in said medicated plaster to said layer of hydrogel adhesive material, an outer layer secured to said layer of hydrogel adhesive material, said outer layer at least having a border extending outwardly of said center cushion layer, said border having an underside, and a layer of adhesive material on the underside of said border.

21. A medicated pad according to claim 20, wherein said medicament includes salicylic acid.

22. A medicated pad according to claim 20, wherein said medicated plaster is secured at a substantially central position of said layer of hydrogel adhesive material.

23. A medicated pad according to claim 20, further comprising a release liner releasably secured to the underside of said layer of hydrogel adhesive material.

24. A medicated pad according to claim 20, further comprising a release tab releasably secured to an upper surface at one side of at least one of said layer of hydrogel adhesive material and said outer layer.

25. A medicated pad according to claim 20, wherein said layer of hydrogel adhesive material includes a recess at the underside thereof, and said barrier layer and said medicated plaster are positioned at least partially in said recess.

26. A medicated pad according to claim 25, wherein said recess includes a side wall and a bottom wall, said barrier layer is interposed between said bottom wall and said medicated plaster, and said medicated plaster is spaced apart from said side wall of said recess.

27. A medicated pad according to claim 20, wherein said recess includes a side wall and a bottom wall, and said barrier layer is interposed between said side and bottom walls of said recess and said medicated plaster.

* * * * *